(12) United States Patent
Sims (10) Patent No.: US 8,272,739 B2
(45) Date of Patent: Sep. 25, 2012

(54) DEVICE AND METHOD FOR CALIBRATING RETINOSCOPES

(76) Inventor: Clinton N. Sims, Fort Myers, FL (US)

(*) Notice: Subject to any disclaimer, the term of this patent is extended or adjusted under 35 U.S.C. 154(b) by 281 days.

(21) Appl. No.: 12/764,216

(22) Filed: Apr. 21, 2010

(65) Prior Publication Data

US 2011/0261323 A1  Oct. 27, 2011

(51) Int. Cl.
*A61B 3/10* (2006.01)
*A61B 3/14* (2006.01)
*A61B 3/00* (2006.01)
(52) U.S. Cl. .................. 351/221; 351/208; 351/246
(58) Field of Classification Search .................. 351/208, 351/218, 221, 246
See application file for complete search history.

(56) References Cited

U.S. PATENT DOCUMENTS

| 3,597,051 A | 8/1971 | Copeland |
| 5,430,508 A | 7/1995 | Sims |
| 5,500,698 A | 3/1996 | Sims |
| 5,650,839 A | 7/1997 | Sims |
| 6,708,597 B2* | 3/2004 | Meyers et al. ............... 89/41.19 |

* cited by examiner

*Primary Examiner* — Jack Dinh
(74) *Attorney, Agent, or Firm* — The Livingston Firm; Edward M. Livingston, Esq.; Bryan L. Loeffler, Esq.

(57) ABSTRACT

A device for calibrating retinoscopes for diverging and/or converging streak and spot retinoscopy and a method for calibrating retinoscopes to produce a given convergence or divergence of light emitted from the retinoscope from a fixed retinoscopic working distance to produce a predetermined pupillary reflex endpoint at neutralization of a refractive error, thereby resulting in a more accurate corrective eye prescriptions and evaluation of the visual system.

53 Claims, 8 Drawing Sheets

| Retinoscopic Working Distance (cm) | Sphere Power Required to Calibrate Retinoscope Using Diverging Light (D) | | Required Focal Length of Retinoscopic Light to Calibrate Retinoscope for Converging Infinity Retinoscopy (cm) | |
|---|---|---|---|---|
| | Infinity Retinoscopic Endpoint | +0.50D Retinoscopic Endpoint | +0.50D Retinoscopic Endpoint | +0.75D Retinoscopic Endpoint |
| 50 | +4.00 | +4.50 | 67 | 80 |
| 54 | +3.75 | +4.25 | 73 | 89 |
| 57 | +3.50 | +4.00 | 80 | 100 |
| 62 | +3.25 | +3.75 | 89 | 115 |
| 67 | +3.00 | +3.50 | 100 | 133 |
| 73 | +2.75 | +3.25 | 115 | 161 |
| 80 | +2.50 | +3.00 | 133 | 200 |

DEVICE AND METHOD FOR CALIBRATING RETINOSCOPES

BACKGROUND OF THE INVENTION

This invention relates to devices and methods for measuring and determining the refractive error in eyes and more particularly, a device for calibrating retinoscopes for diverging and/or converging retinoscopy and a method for calibrating retinoscopes using the device.

Retinoscopy is a technique used by practitioners, such as optometrists and ophthalmologists, to obtain an objective measurement of the refractive error of a patient's eyes in order to determine the patient's prescription for spectacles and/or contacts lenses. Varying retinoscopic measurements are frequently obtained with the current retinoscopes. These retinoscopic errors are due the distance between the condensing lens within the retinoscope and filament of the bulb not being standardized and the inability of the examiner to adjust the divergence of the emitted retinoscopy light to their retinoscopic working distance. The divergence of the light rays emitted from all retinoscopes presently on the market is determined by each manufacturer. Subjective refractions using trial frames and phoropters are used as a more accurate alternative for measuring the refractive error. Phoropters are large and expensive pieces of equipment, which means that many practitioners do not have access to them especially in third world countries. Subjective refractions require a feedback from the patient as to whether one lens is clearer than another lens in order to obtain an accurate measurement of the refractive error. Since subjective refractions cannot be used on patients, such as infants, small children, foreign speaking patients and deaf and/mute patients, an objective measurement using retinoscopy is required. Auto-refractors are used frequently in industrialized countries to replace retinoscopy; however the results are inaccurate in many cases, especially in older patients. As a result, many of these patients are dispensed incorrect lenses.

Jack Copeland was the originator of streak retinoscopy as practiced and taught today and designed the Copeland Optec 360 Streak Retinoscope. The technique of streak retinoscopy is illustrated in Videotape No. 5063 for the American Academy of Ophthalmology's Continuing Ophthalmic Video Education series, entitled "Retinoscopy; Plus Cylinder Technique." U.S. Pat. No. 3,597,051 of Copeland illustrates his streak retinoscope assembly which has a thumb-slide adapted to move the power capsule housing the bulb and battery up and down relative to the shaft of the retinoscope. The ridges on the knurl on the power capsule allow one to rotate the power capsule housing the bulb 360°. Advancing the thumb-slide to its upper position causes light rays emanating from the retinoscope to diverge. By contrast convergence of the light rays occurs when thumb-slide is moved to it lower position. The Copeland Optec 360 Streak Retinoscope contains a +20.00 D condensing lens and a bi-pin lamp. When the thumb-slide is in its upper position, the filament of the lamp is less than five centimeters from the condensing lens and the rays emanating from the filament and passing through the condensing lens are diverging. Moving the slide to a lower position causes the light rays to converge. The filaments of the light bulbs for the Copeland Optec 360 Streak vary in height which results in differences of the divergence power of the emitted retinoscopic light ranging from 0.00 D to 1.00 D. Many retinoscopes on the market work in the opposite manner as the Copeland Optec 360 in that converging rays are produced when the knurl is in the up position and diverging rays when the knurl is in the down position.

In retinoscopy, the examiner uses a retinoscope to shine light into the patient's eye and observes the retinal reflection which is referred to as a pupillary reflex. While moving the streak of light across the pupil the examiner observes the relative movement of the pupillary reflex as they use a phoropter or manually placed lenses over the eye to "neutralize" the pupillary reflex. Streak retinoscopy uses three images to measure the refractive state of the eye. The first image, Image $I_1$ is the luminous streak of the retinoscopic bulb. The second image, Image $I_2$, is the focus or non-focus of image $I_1$ onto the reflecting membrane of the retina. The reflection of the Image $I_2$ produces a third image, Image $I_3$, the pupillary reflex. The non-focus light of Image $I_1$ on the iris is the intercept. The examiner can only see the intercept and the Image $I_3$. The examiner draws all signals from the intercept and third image, Image $I_3$, as when to rotate the pupillary reflex to align the astigmatic axis and to add or subtract lenses (+ or −) to neutralize a refractive error. The retinoscopic working distance is the distance between the luminous filament of the light bulb from the pupillary plane of the eye. Clinically, the retinoscopic working distance in conventional retinoscopy is manually measured with a string from the examiner's nose to the spectacle lens plane in the phoropter or trial frame. The principals of spot retinoscopy are the same as streak retinoscopy; the only difference is the pupillary streak is a spot of light instead of a streak. Streak retinoscopy is popular in the United States, South America and Canada and spot retinoscopy in the European countries.

In retinoscopy, upon neutralization of the refractive error, the diverging retinoscopic light rays used in streak and spot retinoscopy are focused into the eye with a spherical lens placed in front of the eye. This spherical lens is called a retinoscopic spherical lens or fogging lens and its focal length is equal to the examiner's retinoscopic working distance. A neutrality reflex, indicating neutralization of the refractive error, occurs when emitted retinoscopic light exits the retinoscopic spherical lens and enters the pupil as parallel light rays and is focused onto the reflecting membrane of the retina. The reflected light then exits the eye as parallel light rays and is focused by the retinoscopic spherical lens into the hole of a mirror or surface of a semi-reflecting mirror within the retinoscope. This endpoint is called "gross retinoscopy." "Net retinoscopy" occurs on removing the retinoscopic spherical lens, thereby allowing the patient's visual focal point to be extended from the mirror to the end of the refracting lane. If the focal lengths of the retinoscopic working distance, the retinoscopic spherical lens and the emitted diverging retinoscopic light are not equal, the pupillary image will be focused in front or behind the mirror, creating myopic and hyperopic retinoscopic errors respectively. When the pupillary reflex is refocused to the hole in the mirror by the retinoscopist to obtain an infinity pupillary reflex, myopic and hyperopic retinoscopic errors are created.

The variability of conventional retinoscopy is due to several factors, which include the exponentially expanding and moving pupillary reflex which becomes infinite and cannot be seen at neutralization of the patient's refractive error, the low luminosity of the pupillary reflex created by the diverging retinoscopic light which is not calibrated to the examiner's retinoscopic working distance and/or the focal length of the retinoscopic spherical lens. Accommodation and pupillary constriction induced by the retinoscopic light, whether on or off-axis, further reduce the illumination of the pupillary reflex. Retinoscopy through dilated pupils induces optical aberrations and peripheral movements that are different and more myopic than the central pupillary reflex. These factors make it difficult to recognize a definitive endpoint and have contributed to the variability and inaccuracy of conventional retinoscopy.

Retinoscopists use a meridional straddle to confirm the accuracy of the retinoscopic endpoint in conventional retinoscopy. The quote below is from the editorial staff of the American Academy of Pediatrics and Strabismus: "In the 25 years that I taught Retinoscopy and in the 45 years that Copeland taught the subject, calibration of the Scope was to be avoided. Why? Because the endpoint did not depend on calibration of the instrument but rather meridional comparison and ability to utilize all of the various steps together to get to the working distance endpoint."

The reason that an accurate meridional straddle with conventional retinoscopy is important is due to the fact that the endpoint image signifying neutralization of the refractive error cannot be seen when focused into the hole in the mirror or mirror. A meridional balance is when the myopic pupillary reflex is under corrected 0.50 D to create a hyperopic pupillary reflex, which is easily seen and then overcorrected 0.50 D to create a myopic reflex. This process is repeated several times during a retinoscopic examination. Most retinoscopists use the hyperopic reflex as their endpoint which under-corrects the retinoscopic endpoint. As previously described myopic and hyperopic retinoscopic errors occur when the divergence power of the emitted retinoscopic light is not neutralized by the power of the retinoscopic spherical lens and the retinoscopic working distance not being equal to the focal length of the retinoscopic spherical lens. If these three variables are not equal, the retinoscopic endpoint is focused in front of the mirror or beyond the mirror in which case the meridional balance only confirms the accuracy or inaccuracy of the retinoscopic endpoint. The accuracy of the spherical retinoscopic measurement is dependent on the three variables being equal. Statistically, the inaccuracy of the spherical retinoscopic measurement as compared to the measurements of the cylinder and axis supports this theory.

To improve the endpoints of conventional retinoscopy and eliminate other optical problems of conventional retinoscopy Boeder and Kolder developed a retinoscopic technique using parallel light rays emanating from the retinoscope and claimed this produced "neutralization at infinity" or the ability of the patient to read the Snellen chart during retinoscopy. In their formula describing neutralization at infinity, emmetropia or RSR=1 was achieved when the relative speed of movement of the intercept and pupillary reflex were equal and the pupillary reflex was no less than 2.0 mm. This is expressed in the following formula:

$$RSR=[1-t/I_1]/[1+t/I_3]=1$$

RSR=relative speed of pupillary reflex
$I_1$=focal length of Image $I_1$
$I_3$=focal length of Image $I_3$
t=retinoscopic distance (cm)
Image $I_1$=luminous filament of the bulb
Image $I_3$=pupillary reflex is the reflection of the retinoscopic light Unfortunately, their technique required the retinoscopist to recognize the width of a 2.5 mm with-motion pupillary streak as the endpoint, or one no less than 2 mm, an unfamiliar unit of measurement to retinoscopists and many of their claims are invalid:

1. The premise that their infinity retinoscopic technique placed the endpoint of neutralization at infinity instead of the aperture of the retinoscope.
2. The intercept and pupillary reflex will move at different speeds if infinity neutralization is not achieved. That is, if $I_3$ is on the myopic side of neutralization, the with-motion pupillary reflex $I_3$ moves slightly ahead of the intercept and slower if $I_3$ is on the hyperopic side of neutralization.
3. At infinity neutralization, the power of Image $I_3$ is independent of the retinoscopic working distance.
4. The pupillary reflex is characterized by "well defined borders" and "evenly distributed brightness" only at neutralization.
5. The endpoint of infinity retinoscopy or emmetropia occurs only when $I_1=I_3$ is incorrect since in converging infinity retinoscopy, $I_1$ can be greater or less or equal to $I_3$ when emmetropia is obtained.
6. Naming the article "Neutralization at Infinity in Streak Retinoscopy" since neutralization occurs at the examiner's retinoscopic working distance, not infinity.
7. In the derivation of the infinity formula, Image $I_1$ and $I_3$ are located at the position where the retinoscope is located, not beyond the retinoscope and this makes RSR=∞, not 1, when parallel light rays are emitted from the retinoscope.
8. The formula $RSR=[1-t/I_1]/[1+t/I_3]=1$ does not apply to parallel light emitted from the retinoscope, since the formula is derived on the assumption that the focal lengths $I_1$ and $I_3$ will be greater than t, the retinoscopic working distance. In contrast, with parallel light emitted from the retinoscope, RSR is equal to 1 and t is equal to the focal length of $I_1$ and $I_3$.

On an inter-national scale, the average optical remake of spectacle lenses is 6-10%. These lenses are remade at no cost to the patient. This extrapolates to a financial and efficiency loss to the physician and optical shop as well as a reduction of the patient's opinion of the professional skills obtained in that office. The optical remakes and complaints have not been reduced by the auto-refractors or the present day refraction and/or retinoscopic techniques.

Therefore, a need exists for a device and method that eliminates many of the factors responsible for the variability and retinoscopic errors of conventional retinoscopy. More specifically, a need exists for a calibration technique calibrating a retinoscope to the examiner's retinoscopic working distance using either converging or diverging light emanating from the retinoscope.

The relevant prior art includes the following references (U.S. unless stated otherwise):

| Pat. No. | Inventor | Issue/Publication Date |
| --- | --- | --- |
| 5,650,839 | Sims | Jul. 22, 1997 |
| 5,500,698 | Sims | Mar. 19, 1996 |
| 5,430,508 | Sims | Jul. 4, 1995 |
| 3,597,051 | Copeland | Aug. 3, 1971 |

SUMMARY OF THE INVENTION

The primary objective of the present invention is to improve the accuracy of streak and spot retinoscopy using diverging retinoscopic light rays and converging infinity retinoscopy using converging rays. Infinity retinoscopy is equivalent to "net retinoscopy".

Another objective of the present invention is to provide standardization for retinoscopic endpoints using either converging or diverging light emanating from the retinoscope.

Another objective of the present invention is to improve the accuracy and repeatability of measurements using retinoscopy.

An even further objective of the present invention is to provide more accurate endpoints for retinoscopes which use converging and diverging light rays.

Another objective of the present invention is to decrease the need to dilate patient's pupils for retinoscopy.

Another objective of the present invention is to eliminate the potential errors prevalent in conventional retinoscopy as practiced today.

Another objective of the present invention is to provide a brighter and more defined endpoint through the use of converging and diverging retinoscopic light rays.

Another objective of the present invention is to eliminate the need of a retinoscopic fogging or spherical lens.

An even further objective of the present invention is to eliminate the need to perform a meridional straddle.

An even further objective of the present invention is to improve the accuracy of the meridional straddle if performed.

An even further objective of the present invention is to allow a practitioner to obtain more accurate retinoscopic measurements from patients who cannot communicate with the practitioner.

An even further objective of the present invention is to reduce the amount of follow-up appointments for spectacle re-checks due to inaccurate measurements.

An even further objective of the present invention is to provide a quick accuracy check of a patient's glasses.

Another objective of the present invention is to provide a method that is easy to teach to technicians and easy to learn.

The present invention fulfills the above and other objectives by providing an infinity retinoscopic technique using converging rays emitted from the retinoscope and improving the accuracy of retinoscopy which uses diverging rays emitted from the retinoscope by calibrating a manual retinoscope to produce a given convergence or divergence of light ("Image $I_1$") emitted from the retinoscope from a fixed retinoscopic working distance ("t") to produce a predetermined pupillary reflex endpoint ("Image $I_3$") at neutralization of the refractive error.

Improvement in the accuracy of conventional retinoscopy using diverging light rays can be accomplished by adjusting the divergence of the emitted retinoscopic light to neutralize the power of the retinoscopic fogging lens and using a lens whose focal length is equal to the examiner's retinoscopic working distance. From the following formula, the required divergence of the emitted retinoscopic light can be determined to produce an infinity endpoint pupillary reflex or a +0.50 D with-motion endpoint pupillary reflex for one's retinoscopic working distance.

$$2RL + \text{Image } I_1 + \text{Image } I_3 = t$$

Image $I_1$=vergence power of light rays emitted from retinoscope
Image $I_3$=power of pupillary reflex
t=retinoscopic working distance expressed in diopters
RL=retinoscopic fogging lens The steps for calibrating a retinoscope for diverging retinoscopy are as follows.
1. First, a circumferential line is made in the knurl area of the power capsule.
2. Next, the examiner's working distance is optically measured by focusing a retinoscope into an emmetropic eye from their retinoscopic working distance by moving the thumb-slide on the retinoscope until a neutrality reflex occurs, holding the thumb-slide in place, focusing the retinoscopic streak onto a wall and measuring the distance between the retinoscope and the wall.
3. With the aid of the calibration chart, the examiner's retinoscopic working distance is matched to the required calibration spherical lens to be placed in front of the retinoscope for calibrating the divergence of the emitted retinoscopic light rays to the examiner's retinoscopic working distance for an infinity or a +0.50 D retinoscopic endpoint.
4. The retinoscope is then held from a wall a distance equal to the examiner's retinoscopic working distance and the calibration sphere held in front of the retinoscope.
5. The thumb-slide is held in its maximal upward position and the diverging light directed or shined through the calibration sphere onto the wall. The light rays are made less diverging by moving the thumb-slide downward until the retinoscopic streak is focused on the wall.
6. When the retinoscopic streak or spot is focused, the thumb slide is held in this position and the infinity or +0.50 D calibration plate adjusted on the body of the retinoscope to align the alignment line on the plate with the calibration line above the knurl and then secured into position. The divergence of the emitted retinoscopic light for an infinity or a +0.50 D retinoscopic endpoint is now calibrated to the examiner's retinoscopic working distance.
7. After calibration of the retinoscope, the slide bar can be adjusted to maintain the thumb-slide in a fixed position to maintain the calibration of the retinoscope for future retinoscopies.

If the light rays need to be made more diverging to focus the retinoscopic streak onto the wall, the light bulb within the retinoscope is advanced towards the condensing lens to increase the divergence of the emitted retinoscopic light and the above procedures repeated.

Converging infinity retinoscopy eliminates many of the factors responsible for the retinoscopic errors made using conventional retinoscopy. For converging infinity retinoscopy, the required convergence of the emitted retinoscope light to produce a given endpoint pupillary reflex measured in diopters is determined from the following formula:

$$\text{Image } I_1 + \text{Image } I_3 = t$$

Image $I_1$=vergence power of light rays emitted from retinoscope
Image $I_3$=power of pupillary reflex
t=retinoscopic working distance in diopters The steps for calibrating a retinoscope for converging retinoscopy are:
1. A circumferential calibration line in the knurl area of the power capsule which is moved up and down by the thumb-slide.
2. Next, the examiner's retinoscopic working distance is optically measured by focusing a retinoscope into an emmetropic eye from one's retinoscopic working distance by moving the thumb-slide on the retinoscope until a neutrality reflex occurs and then holding the thumb-slide in place. The retinoscopic light is then focused onto a wall and the distance between the retinoscope and the wall measured.
3. With the calibration chart, the examiner's retinoscopic working distance is matched to the required focal length of the retinoscopic light for performing +0.50 D or +0.75 D converging infinity retinoscopy.
4. Next, the retinoscope is placed at the required distance from a wall as specified by the calibration chart, the retinoscopic light rays focused onto the wall and the thumb-slide secured in place.

5. A calibration plate is attached to the side of the retinoscope, aligning the +0.50 D or +0.75 D alignment line with the circumferential calibration line above the knurl to mark the position of the power capsule housing the bulb for future converging infinity retinoscopies.

6. After calibration of the retinoscope, the slide bar can be adjusted to maintain the thumb-slide in a fixed position to maintain the calibration of the retinoscope for future retinoscopies.

The above and other objects, features and advantages of the present invention should become even more readily apparent to those skilled in the art of retinoscopy upon reading the following detailed description in conjunction with the drawings wherein shown and the described illustrative embodiments of the invention.

BRIEF DESCRIPTION OF THE DRAWINGS

FIG. 7-A is an attachable plate for retrofitting a retinoscope for a +0.50 D retinoscopic endpoint using converging rays calibrated to the examiner's retinoscopic working distance;

FIG. 7-B is an attachable plate for retrofitting a retinoscope for a +0.75 D retinoscopic endpoint using converging rays calibrated to the examiner's retinoscopic working distance;

FIG. 7-C is an attachable plate for retrofitting a retinoscope for an infinity retinoscopic endpoint using diverging rays calibrated to the examiner's retinoscopic working distance;

FIG. 7-D is an attachable plate for retrofitting a retinoscope for a +0.50 D retinoscopic endpoint using diverging rays calibrated to the examiner's retinoscopic working distance;

FIG. 8-A is a retinoscope showing proper attachment of the +0.50 D converging plate after calibration of retinoscope light rays to the examiner's retinoscopic working distance;

FIG. 9-A is a retinoscope showing proper attachment of the +0.75 D converging plate after calibration of retinoscopic light rays to the examiner's retinoscopic working distance;

FIG. 10-A is a retinoscope showing proper attachment of the infinity diverging plate after calibration of the retinoscopic light rays to the examiner's retinoscopic working distance;

FIG. 11-A is a retinoscope showing the proper attachment of the +0.50 D diverging plate after calibration of retinoscopic light rays to the examiner's retinoscopic working distance;

| DESCRIPTION OF THE PREFERRED EMBODIMENTS | |
|---|---|
| 1. | retinoscope |
| 2. | thumb-slide |
| 3. | condensing lens |
| 4. | lamp |
| 5. | filament |
| 6. | handle of retinoscope |
| 7. | hole in mirror |
| 8. | mirror |
| 9. | knurl on power capsule |
| 10. | power capsule |
| 11. | calibration line on power capsule |
| 12. | retinoscopic light rays |
| 13. | diverging pattern |
| 14. | converging pattern |
| 15. | optical measurement of retinoscopic working distance: |
| 16. | hold thumb-slide in place and focus retinoscope onto wall. |
| 17. | measure distance between retinoscope and wall |
| 18. | calibration chart |
| 19. | retinoscopic working distance (cm) |
| 20. | calibration sphere required for calibrated infinity endpoint using diverging light rays |
| 21. | calibration sphere required for calibrated +0.50D endpoint using diverging light rays |
| 22. | required focal length of retinoscopic light for +0.50D endpoint using converging light rays |
| 23. | required focal length of retinoscopic light for +0.75D endpoint using converging light rays |
| 24. | plate |
| 25. | +0.50D converging plate |
| 26. | front surface of calibration plate |
| 27. | rear surface of calibration plate |
| 28. | alignment line |
| 29. | attachment means |
| 30. | adjustment means |
| 31. | +0.75D converging plate |
| 32. | infinity diverging plate |

DESCRIPTION OF THE PREFERRED EMBODIMENTS

| | |
|---|---|
| 33. | +0.50D diverging plate |
| 34. | optically measure the retinoscopic working distance |
| 35. | Using the calibration chart, match the distance the retinoscope must be held from wall to the retinoscopic working distance |
| 36. | place retinoscope at required distance from a wall |
| 37. | focus retinoscope and hold thumb-slide in place |
| 38. | align the alignment on plate with the calibration line |
| 39. | secure +0.50D converging plate to retinoscope |
| 40. | secure +0.75D converging plate to retinoscope |
| 41. | using calibration chart, match retinoscopic working distance to power of calibration lens required |
| 42. | place retinoscope a distance from a wall equal to the retinoscopic working distance |
| 43. | place calibration sphere in front of retinoscope |
| 44. | if retinoscopic light fails to focus, move bulb towards condensing lens and refocus reflex onto wall |
| 45. | align calibration line with alignment line on the infinity diverging plate |
| 46. | secure infinity diverging plate to retinoscope |
| 47. | align calibration line with alignment line on the +0.50D diverging plate |
| 48. | secure the +0.50D diverging plate to retinoscope |
| 49. | assume one's routine retinoscopic working distance |
| 50. | check alignment of calibration and alignment lines |
| 51. | slide bar |
| 52. | bulb extender |
| 53. | aperture |

Figure 1:
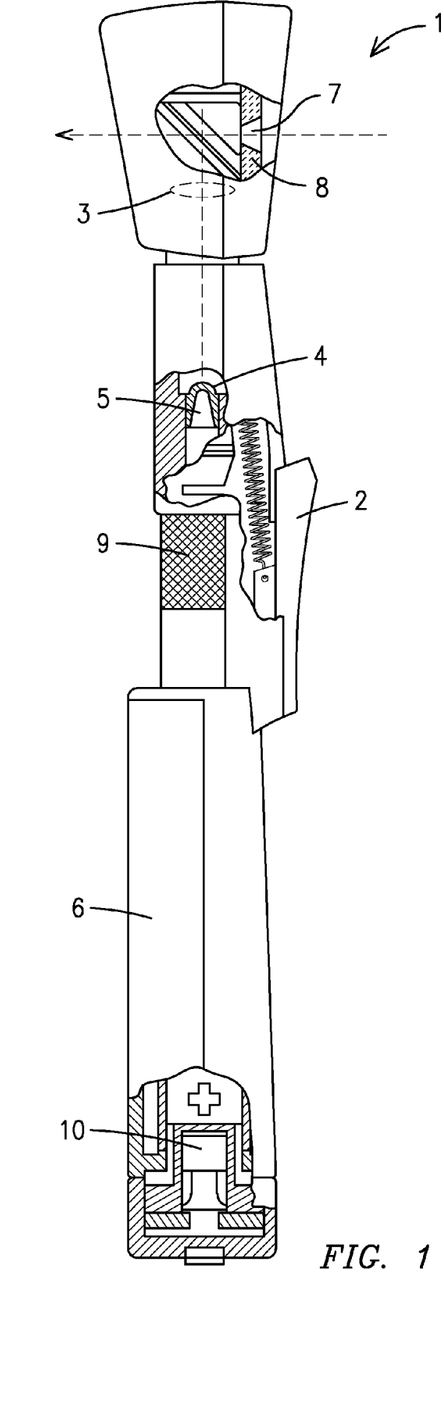
FIG. 1 is a side partial cutaway view of a condensing lens, a mirror, a lamp, a power capsule with a knurl for rotating the power capsule and a thumb-slide which moves the power capsule housing the lamp.

With reference to FIG. 1, a side partial cutaway view of a retinoscope 1 having a thumb-slide 2 and a condensing lens 3 and a lamp 4 is shown. The lamp 4 includes a linear filament 5 designed to create a "streak" image which is reflected from a patient's retina and seen by a practitioner, such as an optometrist or ophthalmologist. The thumb-slide 2 moves the power capsule housing the lamp 4 moves up and down along a handle of the retinoscope 6 so that when the thumb-slide 2 is in a maximal upward position, the filament 5 is less than 5 cm from lens 3 which has an approximate power of +20.00 D. When the thumb-slide 2 is in a maximal down position, the filament 5 is approximately 6.6 cm from the lamp 4. The practitioner can view the light rays reflected from the patient's retina through a small opening 7 in mirror 8. The examiner can only see the retinoscopic light on the patient's iris and the reflected pupillary reflex. The examiner nevertheless is able to move the pupillary reflex toward neutralization by the movement and orientation of the pupillary reflex. The examiner draws all of the retinoscopic signals from the pupillary reflex, that is, when to change or rotate the retinoscopic streak to achieve neutralization of the spherical and cylindrical error.

Figure 2:
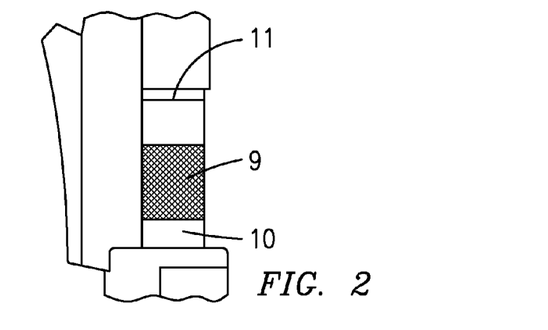
FIG. 2 is a schematic of the knurl area on the power capsule with a circumferential line.

With reference to FIG. 2, calibration of the retinoscope requires a calibration line 11 in the knurl area 9 on the power capsule 10 to align the Plates 7A and 7B for converging infinity retinoscopy and Plates 7C and 7D for diverging retinoscopy after the retinoscope is calibrated to the specifications in the Calibration Chart 18.

Figure 3:
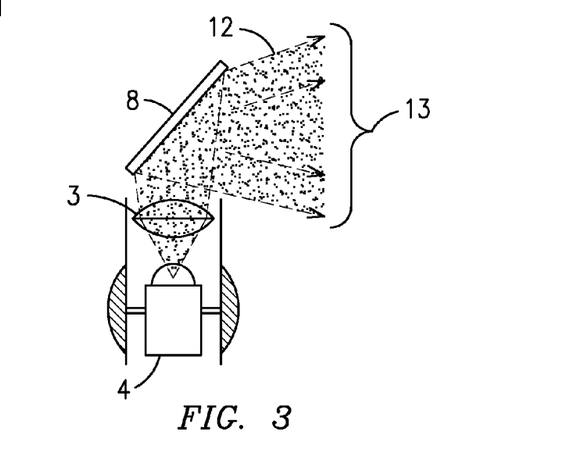
FIG. 3 is a schematic view of light rays emanating from a retinoscope in a diverging pattern.

With reference to FIG. 3, a schematic view of light rays 12 emanating from a retinoscope 1 in a diverging pattern 13 is shown. In diverging retinoscopy the lamp 4 is within the focal length of lens 3. The proximity of the lamp 4 to the lens 3 causes the light rays 12 emitted from the retinoscope 1 to spread out into a diverging pattern 13.

The retinoscopic technique of identifying and neutralizing a refractive error is the same with calibrated diverging retinoscopy as with conventional retinoscopy. Calibrated diverging retinoscopy differs from conventional retinoscopy in that the divergence of the emitted retinoscopic light rays 12 is calibrated to one's retinoscopic working distance. The endpoint of calibrated diverging retinoscopy can be an infinity retinoscopic endpoint which is identical to the endpoint of conventional retinoscopy or a +0.50 D with-motion pupillary reflex.

Figure 4:
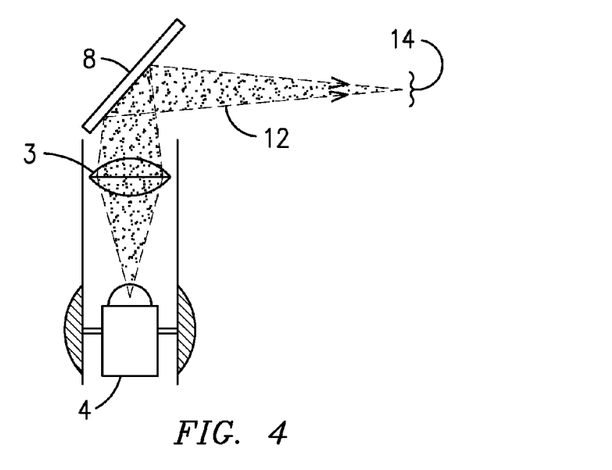
FIG. 4 is a schematic view of light rays emanating from a retinoscope in a converging pattern.

With reference to FIG. 4, a schematic view of light rays 12 emanating from a retinoscope 1 in a converging pattern 14 is shown. In converging retinoscopy, the lamp 4 is displaced beyond the focal length of lens 3. The increased distance of the lamp 4 from the lens 3 causes the light rays 12 emitted from the retinoscope 1 to focus into a converging pattern 14.

Figure 5:
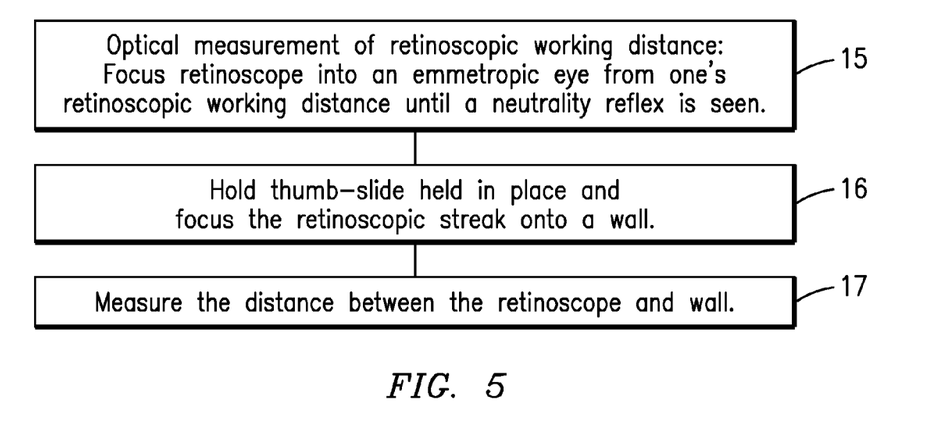
FIG. 5 is a flow chart for optically measuring one's retinoscopic working distance.

With reference to FIG. 5, a flow chart showing the steps for measuring a retinoscopic working distance for use in calibrating a retinoscope for converging and diverging retinoscopy is shown. The examiner's retinoscopic working distance is optically measured by focusing the retinoscopic light into an emmetropic eye using the thumb slide until a neutrality reflex occurs 15. Then, the retinoscopist holds the thumb-slide on the retinoscope in place and the emitted retinoscopic light is focused onto a wall by moving the retinoscope towards the wall until the streak is in focus 16. Finally, the distance between the wall and retinoscope is measured to obtain the examiner's retinoscopic working distance 17.

Figure 6:
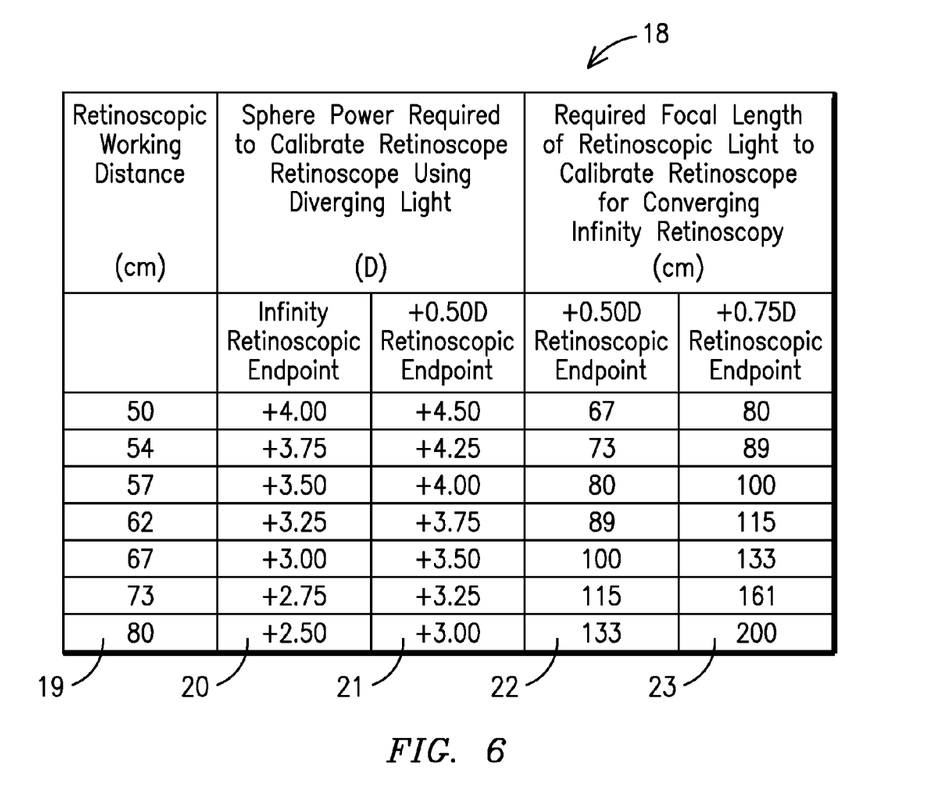
FIG. 6 is a chart for calibrating the retinoscope using diverging rays for an infinity retinoscopic and +0.50 D endpoints and for calibrating a retinoscope using converging rays for +0.50 D and +0.75 D retinoscopic endpoints.
Figure 7A:
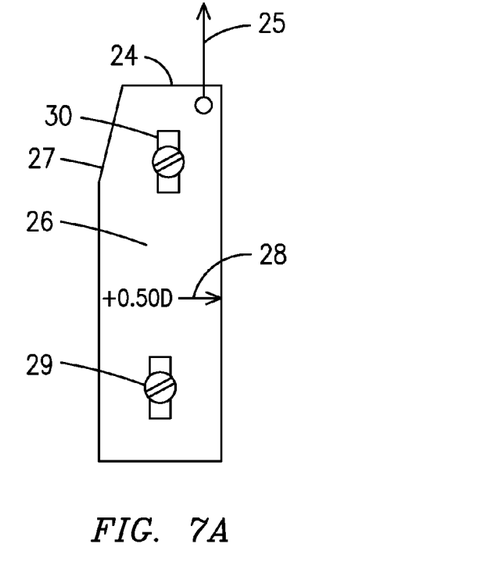
Figure 7B:
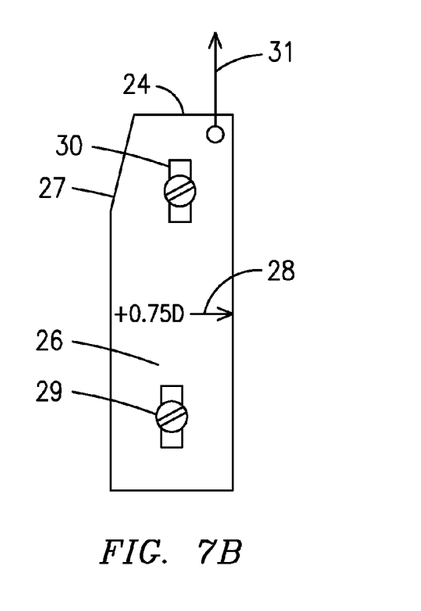
Figure 7C:
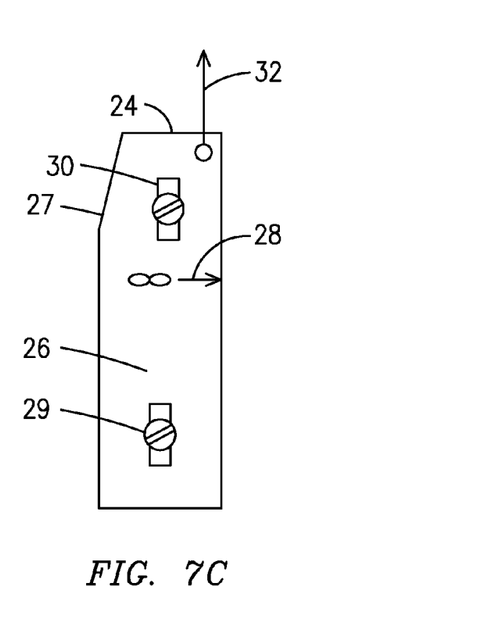
Figure 7D:
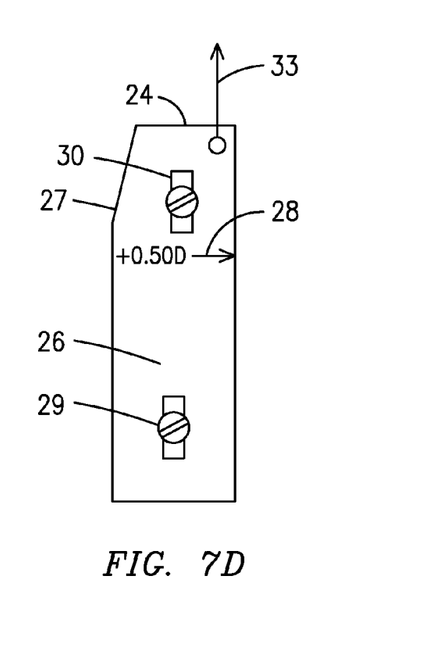

With reference to FIG. 6, a calibration chart 18 is shown. The calibration chart 18 lists the retinoscopic working distance in centimeters 19 and the required power of the calibration lens to be held in front of the retinoscope, which is held from a wall a distance equal to the examiner's retinoscopic working distance 19, in order to calibrated the diverging retinoscopic light for an infinity endpoint 20 and a +0.50 D endpoint 21. Chart 18 also lists the distance a retinoscope must be held from a wall to calibrated the retinoscope using converging light for a +0.50 D endpoint 22 and a +0.75 D endpoint 23, when performing retinoscopy from one's retinoscopic working distance.

With reference to FIG. 7-A, an attachable plate 24 for retrofitting a retinoscope 1 when calibrated for a +0.50 D with-motion endpoint pupillary reflex using converging rays 14 emitted from the retinoscope 1 is shown. The plate 24 shown here is a +0.50 D converging plate 25 and is used when the converging light emanating from the retinoscopies is calibrated for a +0.50 D with-motion retinoscopic endpoint, as shown further in FIG. 8. The +0.50 D converging plate 25 has a front surface 26, a rear surface 27 and an alignment line 28. The plate 24 is attachable to the retinoscope via an attachment means 29, such as screws nuts, etc. The plate 24 is moveable via an adjustment means 30, such as a slot that moves along a screw, so that a user may adjust the alignment line 28 up or down to be in alignment with the calibration line 11 on the power capsule 10. After the retinoscope is calibrated and plate 24 secured into position, the alignment line 28 on plate 24 allows the retinoscopist to know where to place the calibration line 11 on the power capsule 10 to obtain a +0.50 D retinoscopic endpoint using converging light, as shown further in FIG. 8-A.

With reference to FIG. 7-B, an attachable plate 24 for retrofitting a retinoscope 1 when calibrated for a +0.75 D with-motion retinoscopic reflex using converging light rays 14 emitted from the retinoscope 1 is shown. The plate 24 shown here is a +0.75 D converging plate 31 and is used when the converging light 14 emanating from the retinoscope is calibrated for a +0.75 D with-motion retinoscopic endpoint, as shown further in FIG. 9. The +0.75 D converging plate 31 has a front surface 26, a rear surface 27 and an alignment line 28. The plate 24 is attachable to the retinoscope via an attachment means 29, such as screws nuts, etc. The plate 24 is moveable via an adjustment means 30, such as a slot that moves along a screw, so that a user may adjust the alignment line 28 up or down to be in level with the calibration line 11 on the power capsule 10. After the retinoscope is calibrated and plate 24 secured into position, the alignment line 28 on plate 31 allows the retinoscopist to know where to place the calibration line 11 on the power capsule 10 to obtain a +0.75 D retinoscopic endpoint using converging light, as shown further in FIG. 9-A.

With reference to FIG. 7-C, an attachable plate 24 for retrofitting a retinoscope 1 when calibrated for an infinity endpoint using diverging light rays 13 emitted from the retinoscope 1 is shown. The plate 24 shown here is an infinity endpoint diverging plate 32 and is used when the diverging light 13 emitted from the retinoscope is calibrated for an infinity retinoscopic endpoint, as shown further in FIG. 10. The infinity diverging plate 32 has a front surface 26, a rear surface 27 and an alignment line 28. The plate 24 is attachable to the retinoscope via an attachment means 29 such as screws, adhesive, nuts, etc. The plate 24 is moveable via an adjustment means 30, such as a slot that moves along a screw, so that a user may adjust the alignment line 28 up or down to be level with the calibration line 11 on the power capsule 10 after the retinoscope is calibrated. After the retinoscope is calibrated and plate 32 secured into position, the alignment line 28 on plate 32 allows the retinoscopist to know where to place the calibration line 11 on the power capsule 10 to perform retinoscopy with diverging light rays to obtain an infinity retinoscopic endpoint adjusted to one retinoscopic working distance as shown further in FIG. 10-A.

With reference to FIG. 7-D, an attachable plate 24 for retrofitting a retinoscope 1 when calibrated to a +0.50 D with-motion pupillary reflex endpoint using diverging retinoscopic light rays 13 is shown. The plate 24 shown here is a diverging plate 33 and is used when the diverging light emanating from the retinoscope is calibrated for a +0.50 D with motion retinoscopic endpoint as shown further in FIG. 11. The +0.50 D diverging plate 33 has a front surface 26, a rear surface 27 and an alignment line 28. The plate 24 is attachable to the retinoscope via an attachment means 29, such as screws, adhesive, nuts, etc. The plate 24 is moveable via an adjustment means 30, such as a slot that moves along a screw, so that a user may adjust the alignment line 28 up or down to be in alignment with the calibration line 11 on the power capsule 10 after the retinoscope is calibrated. The alignment line 28 on plate 33 allows the retinoscopist to know where to place the calibration line 11 on the power capsule 10 to perform retinoscopy with diverging light rays to obtain a +0.50 D retinoscopic endpoint adjusted to one retinoscopic working distance as shown further in FIG. 11-A.

Figure 8:
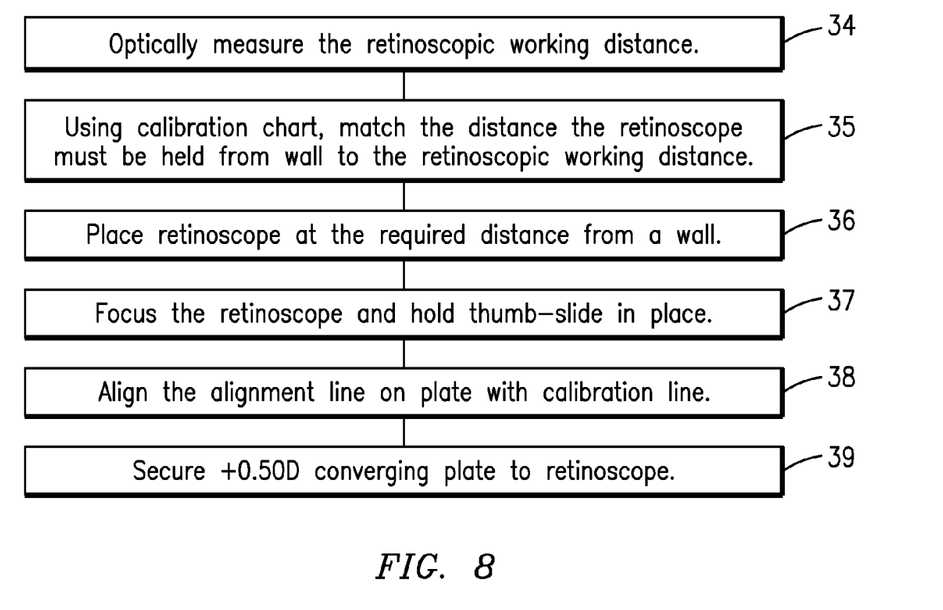
FIG. 8 is a flow chart showing the steps for calibrating a retinoscope for a +0.50 D retinoscopic endpoint using converging retinoscopic light rays calibrated to the examiner's retinoscopic working distance.
Figure 8A:
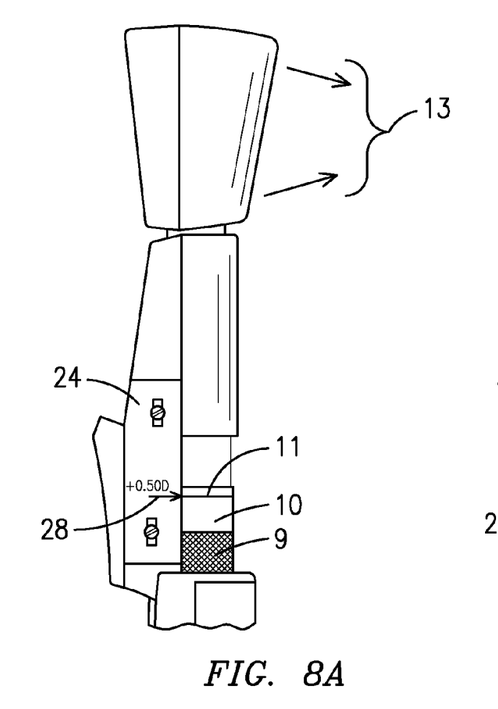

With reference to FIG. 8, a flow chart showing the steps for calibrating a retinoscope for a +0.50 D with-motions retinoscopic endpoint using converging retinoscope light rays 14 is show. First, the retinoscopic working distance is optically measured 34 as shown in FIG. 5. Then, the required focal length of the emitted retinoscope light for a +0.50 D retinoscopic endpoint is determined 35 using the calibration chart 18 illustrated in FIG. 6. For example, if the retinoscopic working distance is 67 cm, the required focal length of the emitted retinoscopic light is 100 cm. Next, the retinoscope is placed at the proper focal length from a wall 36 and focused 37. Finally 38, the alignment line 28 on the +0.50 D converging plate 25 is aligned with the calibration line 11 on the power capsule 10 as shown further in FIG. 8-A and secured 39.

With reference to FIG. 8-A, a retinoscope 1 having a +0.50 D converging plate 25 attached thereto is shown. The retinoscope 1 has been calibrated for a +0.50 D pupillary reflex endpoint using converging retinoscope light rays 14. The technique for performing retinoscope using a retinoscope calibrated for a +0.50 D retinoscopic endpoint is the same as in conventional retinoscopy, except that the calibration line 11 on the power capsule 10 is level with the alignment line 28 on the +050 D converging plate 25 and the retinoscopic endpoint is a +0.50 D with-motion retinoscopic reflex with the +0.50 D pupillary reflex and intercept moving in unison.

Figure 9:
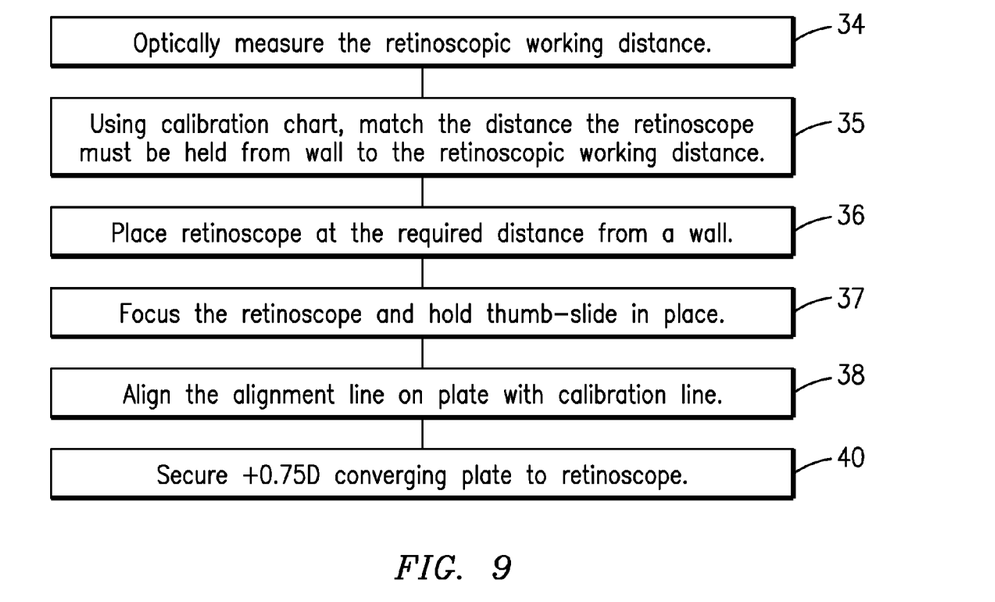
FIG. 9 is a flow chart showing the steps for calibrating a retinoscope for a +0.75 D pupillary reflex endpoint using converging retinoscopic light rays.
Figure 9A:
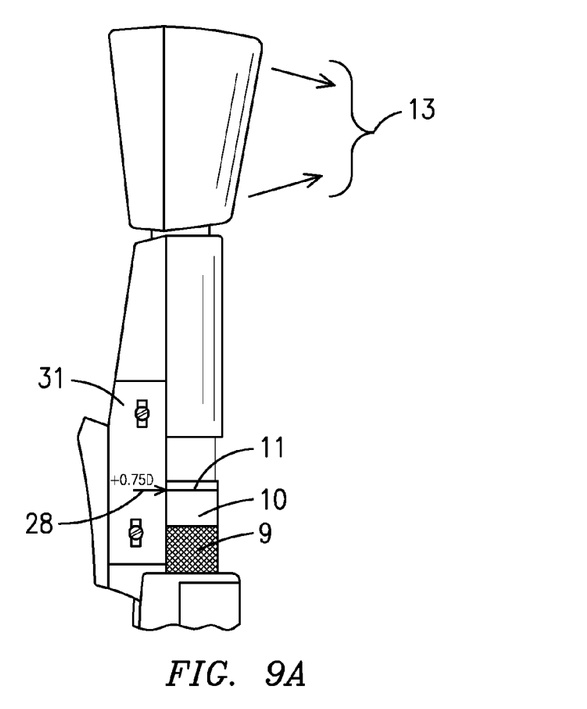

With reference to FIG. 9, a flow chart showing the steps for calibrating a retinoscope for a +0.75 D with-motions retinoscopic endpoint using converging retinoscope light rays 14 is show. First, the retinoscopic working distance is measured 34 as shown in FIG. 5. Then, the required focal length of the emitted retinoscope light is determined 35 using the calibration chart 18 illustrated in FIG. 6. For example, if the retinoscopic working distance is 67 cm, the required focal length of the emitted retinoscopic light is 133 cm. Next, the retinoscope is placed at the proper focal length from a wall 36 and focused 37 and the thumb-slide held in position. Finally 38, the alignment line 28 on the +0.75 D converging plate 31 is aligned with the calibration line 11 on the power capsule 10 of retinoscope 1 as shown further in FIG. 8-A and secured 40.

With reference to FIG. 9-A, a retinoscope 1 having a +0.75 D converging plate 31 attached thereto is shown. The retinoscope 1 has been calibrated for a +0.75 D endpoint using converging retinoscopic light rays 14. The technique for performing retinoscopy using a retinoscope calibrated for a +0.75 D retinoscopic endpoint is the same as in conventional retinoscopy, except the calibration line 11 on power capsule 10 is level with the alignment line 28 on the +075 D converging plate 31 and the retinoscopic endpoint is a +0.75 D retinoscopic and moves in unison with the intercept.

Figure 10:
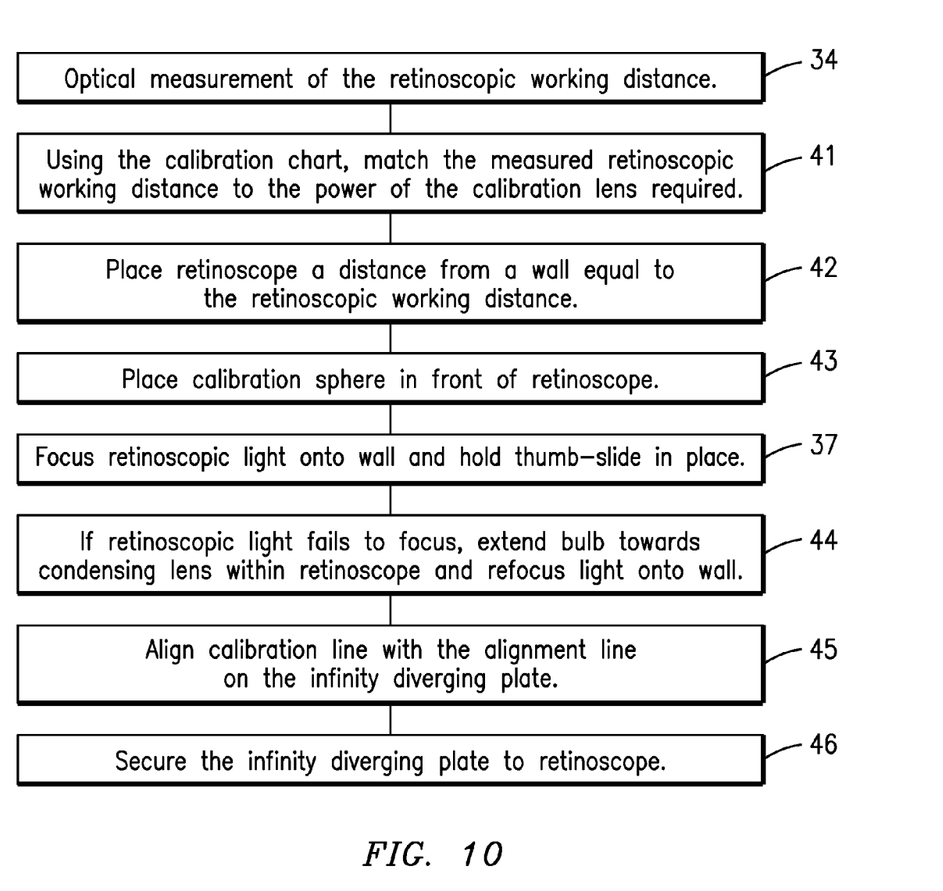
FIG. 10 is a flow chart showing the steps for calibrating a retinoscope for an infinity retinoscopic endpoint using diverging retinoscopic light rays calibrated to the examiner's retinoscopic working distance.
Figure 10A:
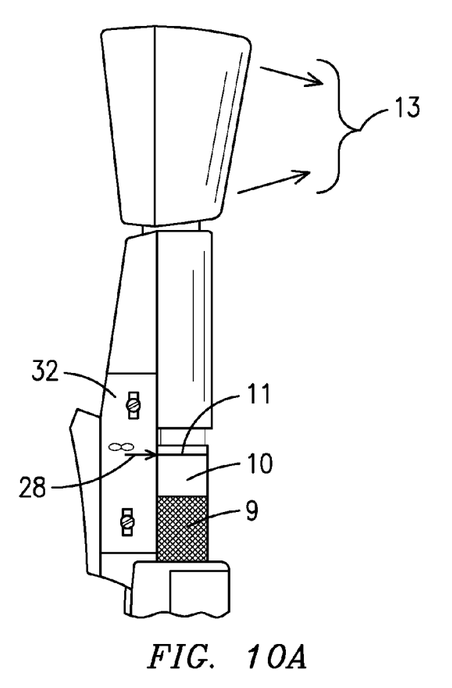

With reference to FIG. 10, a flow chart showing the steps for calibrating a retinoscope 1 for an infinity retinoscopic endpoint using diverging retinoscopic rays 13 is shown. First, the retinoscopic working distance 34 is measured in centimeters, as shown in FIG. 5. Next 41, the retinoscopic working distance in centimeters 19 is matched to the power of the calibration lens required 20 using the calibration chart 18. For example, if the retinoscopic working distance is 67 cm, the power of calibration sphere would be +3.00 D. Next, the retinoscope 1 is placed at a distance from the wall equal to the retinoscopic working distance 42. Next, the +3.00 D calibration sphere as determined from 41 is placed in front of the retinoscope 43. With the thumb-slide 2 in the maximal upward position and the diverging retinoscopic light shinning through the +3.00 D calibration spherical lens, the thumb-slide 2 is lowered until the retinoscopic streak is focused onto the wall 37. If the retinoscopic streak fails to focus onto the wall, the bulb 4 is advanced towards the condensing lens 3 within the retinoscope 1 and the procedure repeated until the retinoscopic streak is focused onto the wall, 44. Next 45, the alignment line 28 on the infinity diverging plate 32 is aligned with the calibration line 11 on the power capsule 10 and secured in position 46 as shown further in FIG. 10-A.

With reference to FIG. 10-A, a retinoscope 1 having an ∞ diverging plate 32 attached thereto is shown. The retinoscope 1 has been calibrated for an infinity retinoscopic endpoint using diverging retinoscope light rays 13. The technique for performing retinoscopy using an infinity retinoscopic endpoint with the emitted retinoscopic light rays calibrated to the examiner's retinoscopic working distance is the same as in conventional retinoscopy, except that the calibration line 11 on the power capsule 10 is level with the measuring line 28 on the infinity plate 32.

Figure 11:
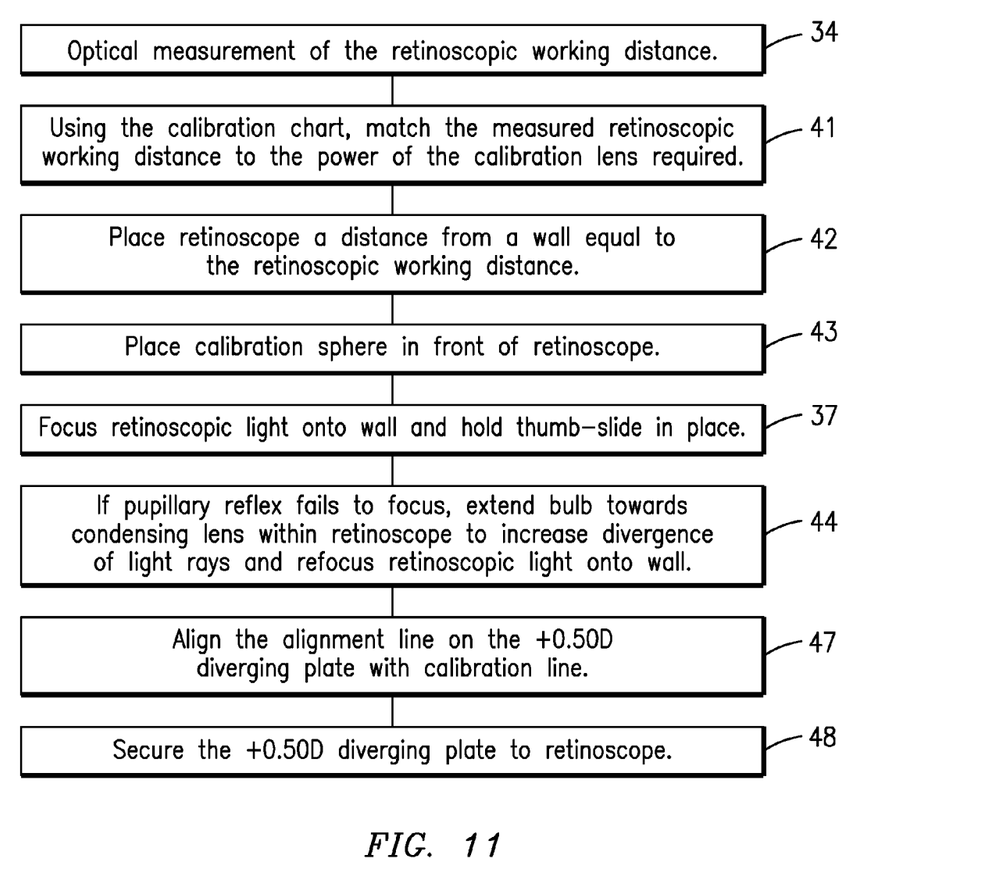
FIG. 11 is a flow chart showing the steps for calibrating a retinoscope for a +0.50 D retinoscopic endpoint using diverging retinoscopic light rays calibrated to the examiner's retinoscopic working distance.
Figure 11A:
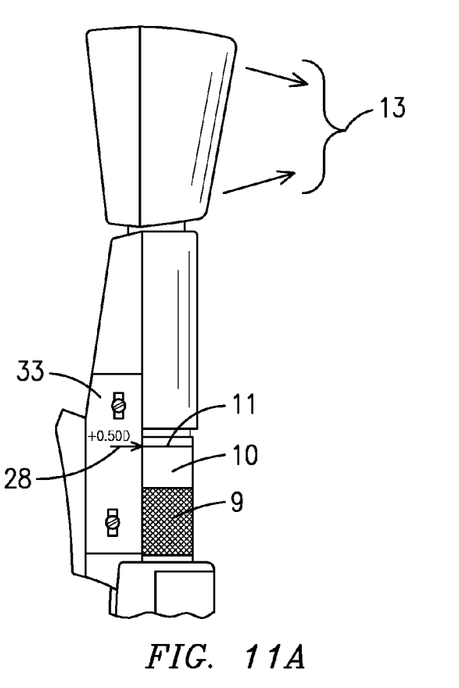

With reference to FIG. 11, a flow chart showing the steps for calibrating a retinoscope 1 for a +0.50 D retinoscopic endpoint using diverging retinoscope light rays 13 is show.

First the working distance is measure centimeters 34, as shown in FIG. 5. Next 41, the retinoscopic working distance in centimeters 19 is matched to the power of the calibration lens required 21 using the calibration chart 18. For example, if the retinoscopic working distance is 67 cm the power of the calibration sphere would be +3.50 D. Next, the retinoscope 1 is placed at a distance from the wall equal to the retinoscopic working distance 42. Next, the +3.50 D sphere is placed in front of the retinoscope 43. With the thumb-slide 2 in the maximal upward position and the diverging retinoscopic light shinning through the +3.50 D calibration lens, the thumb-slide 2 lowered until the retinoscopic streak is focused onto the wall 37. If the retinoscopic streak fails to focus onto the wall, the bulb 4 is displaced toward the +20 D condensing lens 3 within the retinoscope and the procedure repeated until the retinoscopic streak is focused onto the wall, 44. Next 47, the alignment line 28 on +0.50 D diverging plate 33 is aligned with the calibration line 11 on the power capsule 10 and secured in position 48 as shown further in FIG. 11-A.

With reference to FIG. 11-A, a retinoscope 1 having a +0.50 D diverging plate 33 attached thereto is shown. The retinoscope 1 has been calibrated for a +0.50 D retinoscopic endpoint using diverging light rays 13 exiting the retinoscope. The technique for performing retinoscopy using a retinoscope calibrated to one's retinoscopic working distance for a +0.50 D retinoscopic endpoint is the same as conventional retinoscopy except the retinoscopic endpoint is a +0.50 D with-motion retinoscopic endpoint and the calibration line 11 is level with the alignment line 28. In contrast to the +0.50 D retinoscopic endpoint produced with converging rays emitted from the retinoscope in FIG. 8-A, with diverging rays the +0.50 D retinoscopic endpoint moves faster than the intercept.

Figure 12:
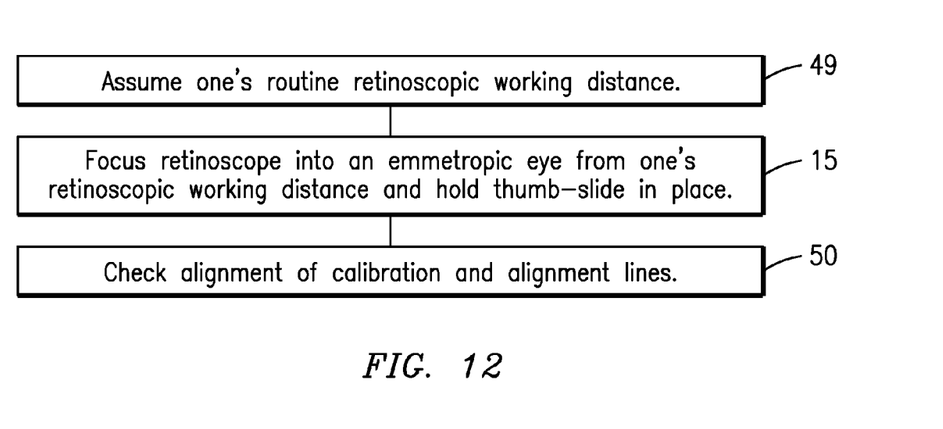
FIG. 12 is a flow chart showing the steps for performing a calibration check of a retinoscope emanating converging rays calibrated to the examiner's retinoscopic working distance.

With reference to FIG. 12, a flow chart showing the steps for performing a calibration check on retinoscopes calibrated to emit converging rays 14 as shown in FIGS. 8-A and 9-A is shown. First, the practitioner assumes his or her routine retinoscope distance 49. Then the practitioner lowers the thumb-slide 2 of the retinoscope from its maximal upward position until a neutrality reflex is seen in an emmetropic eye 12 and holds the thumb-slide in this position 15. If the calibration line 11 on the power capsule 10 is level with the alignment line 28 on the converging plates 25 or 31, the retinoscope is calibrated 50. In the Copeland Optec 360 Streak Retinoscope, the thumb-side is kept in the most superior position by a spring.

Figure 13:
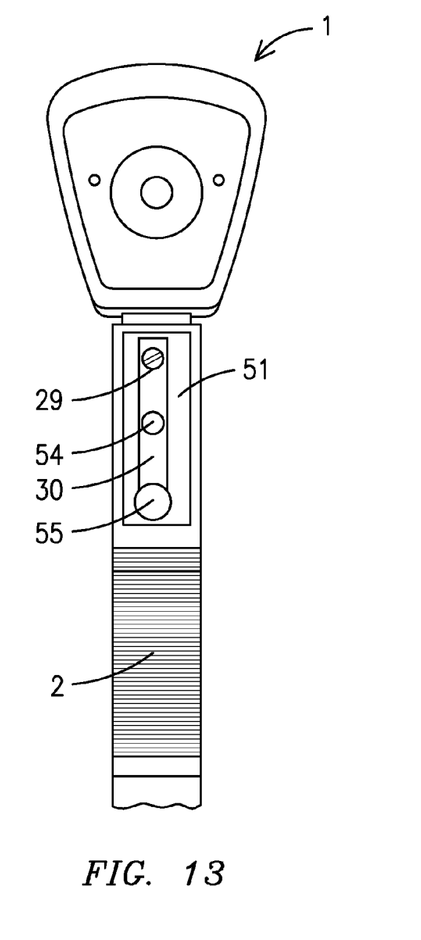
FIG. 13 is a retinoscope showing a slide bar which can be adjusted to maintain the thumb-slide in a fixed position to maintain the calibration of the retinoscope for future retinoscopies.

With reference to FIG. 13, a retinoscope 1 having a slide bar 51 attached to the body of the retinoscope and locate superiorly to the thumb-slide 2 thereto is shown. The slide bar 51 is attachable to the retinoscope via an attachment means 29, such as screws, nut, etc. The slide bar 51 is moveable via an adjustment means 30, such as a slot that moves along a screw. After the retinoscope is calibrated, the slide bar 51 is adjusted to touch the top of the thumb-slide 2 to prevent it from moving upward and secured to the retinoscope.

Although a practitioner may use a +0.50 D retinoscopic endpoint or a +0.75 D retinoscopic endpoint, the +0.50 D retinoscopic endpoint is easier, faster and more convenient to confirm than the +0.75 D retinoscopic endpoint, since during retinoscopy, the neutrality reflex is displaced 2 lenses from the +0.50 D retinoscopic endpoint and 3 lenses from the +0.75 D retinoscopic endpoint.

Figure 14:
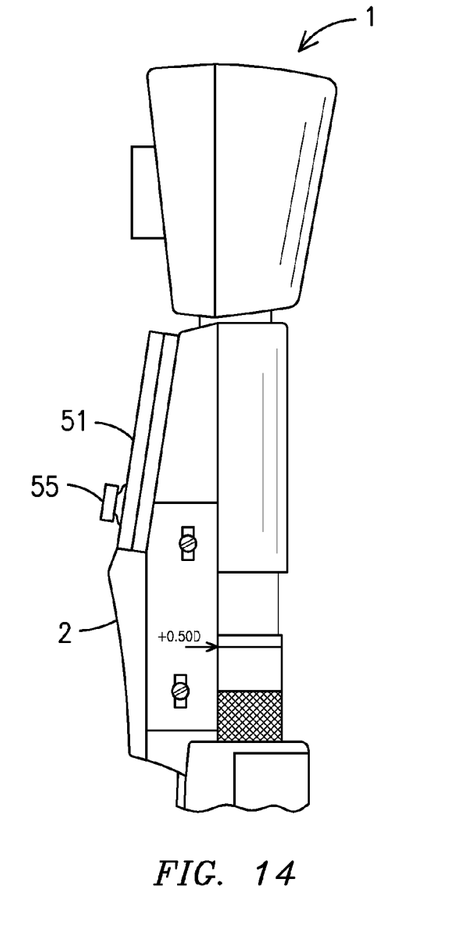
FIG. 14, a front perspective view of a bulb extender 52 of the present invention.
Figure 15:
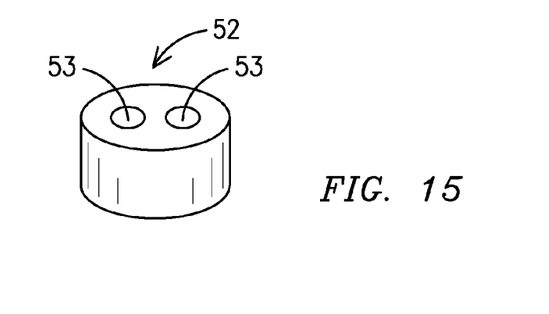

Finally with reference to FIG. 14, a front perspective view of a bulb extender 52 of the present invention is shown. The bulb extender 52 acts as a spacer to increase the height of a lamp 4 and filament 5 within the retinoscope 1. The bulb extender 52 elevates lamps 4 having shorter filaments 5 towards the lens 3 in order to increase the divergence of emitted retinscopic light. The bulb extender 52 has at least one aperture 53 to allow electronic communication between a power source of the retinoscope 1 and the filament 5.

It is to be understood that while a preferred embodiment of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

Having thus described my invention, I claim:

1. A calibration plate for calibrating a retinoscope having a handle, a lamp housed within a power capsule with a calibration line located thereon, a lens located above the lamp, a thumb-slide for sliding the power capsule housing the lamp, said calibration plate comprising:
   a flat piece of material having a front surface and a rear surface;
   at least one calibration line located on the front surface;
   an attachment means for attaching said calibration plate to a side portion of the retinoscope; and
   said calibration plate being capable of sliding up or down via an adjustment means that allows a user to adjust the calibration plate on the retinoscope so the at least one calibration line located on the front surface of the calibration plate is in alignment with the calibration line located on the power capsule.

2. The calibration plate of claim 1 wherein:
   a slide bar attached to the retinoscope and located superiorly to the thumb-slide via an attachment means;
   said slide bar being capable of sliding up or down via an adjustment means that allows a user to position a bottom edge of the slide bar at a predetermined location above the thumb-slide to prevent the thumb-slide from moving higher than the bottom edge of the slide bar.

3. The calibration plate of claim 1 wherein:
   said calibration line is located at a predetermined position on the calibration plate to allow for alignment with the calibration line on the power capsule for calibrating a retinoscope for a +0.50 D visible light streak endpoint using converging retinoscopic light.

4. The calibration plate of claim 1 wherein:
   said calibration line is located at a predetermined position on the calibration plate to allow for alignment with the calibration line on the power capsule for calibrating a retinoscope for +0.75 D visible light streak endpoint using converging retinoscopic light.

5. The calibration plate of claim 1 wherein:
   said calibration line is located at a predetermined position on the calibration plate to allow for alignment with the calibration line on the power capsule for calibrating a retinoscope for +0.50 D visible light streak endpoint using converging retinoscopic light.

6. The calibration plate of claim 1 wherein:
said calibration line is located at a predetermined position on the calibration plate to allow for alignment with the calibration line on the power capsule for calibrating a retinoscope for an infinity neutrality endpoint using diverging retinoscopic light.

7. The calibration plate of claim 1 wherein:
the lamp creates a spot image.

8. The calibration plate of claim 1 wherein:
the lamp creates a streak image.

9. A method for calibrating a retinoscope emitting converging light having a handle, a lamp housed within a power capsule with a calibration line located thereon, a lens located above the lamp, a thumb-slide for sliding the power capsule housing the lamp up or down, a calibration plate slidably attached to a side portion of the retinoscope proximate to the thumb-slide, said calibration plate being constructed from a flat piece of material having a front surface and a rear surface with at least one calibration line located on the front surface; said method comprising the following steps:
  a. measuring one's retinoscopic working distance using the retinoscope;
  b. from calibration chart determining required focal length of the retinoscopic light with said retinoscopic working distance;
  c. placing the retinoscope at a distance from a wall that's equal to the focal length of the retinoscopic light; and
  d. aligning the calibration line on the calibration plate with the calibration line on the power capsule.

10. The method of claim 9 wherein step a comprises the following steps:
  a. focusing the retinoscopic light into an emmetropic eye;
  b. adjusting the position of the retinoscope to focus the retinoscopic light emanating from the retinoscope onto a wall; and
  c. measuring the distance between the retinoscope and the wall.

11. The method of claim 9 wherein step e further comprises the following step:
adjusting the placement of the calibration plate on the retinoscope so that the calibration line on the calibration plate is even with the calibration line on the power capsule housing the lamp.

12. The method of claim 9 further comprising the following steps after d of:
  a. assuming a routine retinoscopic working distance;
  b. adjusting the thumb-slide until a neutrality reflex is seen in the patient; and
  c. checking that the calibration line on the calibration plate is even with the calibration line on the power capsule housing the lamp.

13. The method of claim 9 wherein:
if the working distance equals 50 cm then the required focal length of the retinoscopic light will equal 67 cm for calibrating the retinoscope to perform +0.50 D converging retinoscopy.

14. The method of claim 9 wherein:
if the working distance equals 54 cm then the required focal length of the retinoscopic light will equal 73 cm for calibrating the retinoscope to perform +0.50 D converging retinoscopy.

15. The method of claim 9 wherein:
if the working distance equals 57 cm then the required focal length of the retinoscopic light will equal 80 cm for calibrating the retinoscope to perform +0.50 D converging retinoscopy.

16. The method of claim 9 wherein:
if the working distance equals 62 cm then the required focal length of the retinoscopic light will equal 89 cm for calibrating the retinoscope to perform +0.50 D converging retinoscopy.

17. The method of claim 9 wherein:
if the working distance equals 67 cm then the required focal length of the retinoscopic light will equal 100 cm for calibrating the retinoscope to perform +0.50 D converging retinoscopy.

18. The method of claim 9 wherein:
if the working distance equals 73 cm then the required focal length of the retinoscopic light will equal 115 cm for calibrating the retinoscope to perform +0.50 D converging retinoscopy.

19. The method of claim 9 wherein:
if the working distance equals 80 cm then the required focal length of the retinoscopic light will equal 133 cm for calibrating the retinoscope to perform +0.50 D converging retinoscopy.

20. The method of claim 9 wherein:
if the working distance equals 50 cm then the required focal length of the retinoscopic light will equal 80 cm for calibrating the retinoscope to perform +0.75 D converging retinoscopy.

21. The method of claim 9 wherein:
if the working distance equals 54 cm then the required focal length of the retinoscopic light will equal 89 cm for calibrating the retinoscope to perform +0.75 D converging retinoscopy.

22. The method of claim 9 wherein:
if the working distance equals 57 cm then the required focal length of the retinoscopic light will equal 100 cm for calibrating the retinoscope to perform +0.75 D converging retinoscopy.

23. The method of claim 9 wherein:
if the working distance equals 62 cm then the required focal length of the retinoscopic light will equal 115 cm for calibrating the retinoscope to perform +0.75 D converging retinoscopy.

24. The method of claim 9 wherein:
if the working distance equals 67 cm then the required focal length of the retinoscopic light will equal 133 cm for calibrating the retinoscope to perform +0.75 D converging retinoscopy.

25. The method of claim 9 wherein:
if the working distance equal 73 cm then the required focal length of the retinoscopic light will equal 161 cm for calibrating the retinoscope to perform +0.75 D converging retinoscopy.

26. The method of claim 9 wherein:
if the working distance equals 80 cm then the required focal length of the retinoscopic light will equal 200 cm for calibrating the retinoscope to perform +0.75 D converging retinoscopy.

27. The method of claim 9 wherein:
the lamp creates a spot image.

28. The method of claim 9 wherein:
the lamp creates a streak image.

29. The method of claim 9 further comprising the following steps after d of:
  locking at least one slide lock on the retinoscope to prevent the thumb-slide from sliding past a predetermined point.
30. The method of claim 9 further comprising the step of:
  placing a bulb extender under the lamp in order to elevate the lamp towards the lens and increase divergence of emitted retinsocopic light.
31. A method for calibrating a retinoscope emitting diverging light having a handle, a lamp housed within a power capsule with a calibration line located thereon, a lens located above the lamp, a thumb-slide for sliding the power capsule housing the lamp up or down, a calibration plate slidably attached to a side portion of the retinoscope proximate to the thumb-slide, said calibration plate being constructed from a flat piece of material having a front surface and a rear surface with at least one calibration line located on the front surface; said method comprising the following steps:
  a. measuring one's retinoscopic working distance using the retinoscope;
  b. determining an equivalent sphere with same focal length equal to retinoscopic working distance;
  c. placing the retinoscope at a distance from a wall equal to the focal length;
  d. placing a sphere with twice the power determined in step b in front of the retinoscope;
  e. focusing the retinoscope; and
  f. placing the calibration line on the calibration plate even with the calibration line on power capsule housing the lamp.
32. The method of claim 31 wherein step a comprises the following steps:
  a. focusing the retinoscope into an emmetropic eye;
  b. adjusting the position of the retinoscope to focus the retinoscopic light emanating from the retinoscope onto a wall; and
  c. measuring the distance between the retinoscope and the wall.
33. The method of claim 31 wherein step f further comprises the following step:
  adjusting the placement of the calibration plate on the retinoscope so that the alignment line is even with the calibration line on the power capsule housing the lamp.
34. The method of claim 31 wherein:
  if the working distance equals 50 cm, then the sphere power will equal +4.00 D for calibrating the retinoscope to perform diverging retinoscopy with an infinity endpoint.
35. The method of claim 31 wherein:
  if the working distance equals 54 cm, then the sphere power will equal +3.75 D for calibrating the retinoscope to perform diverging retinoscopy with an infinity endpoint.
36. The method of claim 31 wherein:
  if the working distance equals 57 cm, then the sphere power will equal +3.50 D for calibrating the retinoscope to perform diverging retinoscopy with an infinity endpoint.
37. The method of claim 31 wherein:
  if the working distance equals 62 cm, then the sphere power will equal +3.25 D for calibrating the retinoscope to perform diverging retinoscopy with an infinity endpoint.
38. The method of claim 31 wherein:
  if the working distance equals 67 cm, then the sphere power will equal +3.00 D for calibrating the retinoscope to perform diverging retinoscopy with an infinity endpoint.
39. The method of claim 31 wherein:
  if the working distance equals 73 cm, then the sphere power will equal +2.75 D for calibrating the retinoscope to perform diverging retinoscopy with an infinity endpoint.
40. The method of claim 31 wherein:
  if the working distance equals 80 cm, then the sphere power will equal +2.50 D for calibrating the retinoscope to perform diverging retinoscopy with an infinity endpoint.
41. The method of claim 31 further comprising the following steps after f of:
  a. assuming a routine retinoscopic working distance;
  b. placing a sphere with a focal length equal to the retinoscopic working distance in front of an emmetropic eye;
  c. adjusting the thumb-slide until a neutrality reflex is seen in the patient; and
  d. checking that the calibration line on the calibration plate is level with the calibration line on the power capsule.
42. The method of claim 31 wherein:
  if the working distance equals 50 cm, then the sphere power will equal +4.50 D for calibrating the retinoscope to perform diverging retinoscopy with a +0.50 D endpoint.
43. The method of claim 31 wherein:
  if the working distance equals 54 cm, then the sphere power will equal +4.25 D for calibrating the retinoscope to perform diverging retinoscopy with a +0.50 D endpoint.
44. The method of claim 31 wherein:
  if the working distance equals 57 cm, then the sphere power will equal +4.00 D for calibrating the retinoscope to perform diverging retinoscopy with a +0.50 D endpoint.
45. The method of claim 31 wherein:
  if the working distance equals 62 cm, then the sphere power will equal +3.75 D for calibrating the retinoscope to perform diverging retinoscopy with a +0.50 D endpoint.
46. The method of claim 31 wherein:
  if the working distance equals 50 cm, then the sphere power will equal +4.50 D for calibrating the retinoscope to perform diverging retinoscopy with a +0.50 D endpoint.
47. The method of claim 31 wherein:
  if the working distance equals 73 cm, then the sphere power will equal +3.25 D for calibrating the retinoscope to perform diverging retinoscopy with a +0.50 D endpoint.
48. The method of claim 31 wherein:
  if the working distance equals 80 cm, then the sphere power will equal +3.00 D for calibrating the retinoscope to perform diverging retinoscopy with a +0.50 D endpoint.
49. The method of claim 31 further comprising the step of:
  adjusting the placement of the calibration plate on the retinoscope so that the calibration line is even with the calibration line on the power capsule housing the lamp.
50. The method of claim 31 wherein:
  the lamp creates a spot image.
51. The method of claim 31 wherein:
  the lamp creates a streak image.
52. The method of claim 31 further comprising the following steps after d of:
  locking at least one slide lock on the retinoscope to prevent the thumb-slide from sliding past a predetermined point.
53. The method of claim 31 further comprising the step of:
  placing a bulb extender under the lamp in order to elevate the lamp towards the lens and increase divergence of emitted retinoscopic light.

* * * * *